United States Patent [19]

Guigan

[11] Patent Number: 4,743,558
[45] Date of Patent: May 10, 1988

[54] METHOD OF PERFORMING MEDICAL ANALYSIS ON A SAMPLE OF LIQUID BY MEANS OF AT LEAST ONE LIQUID REAGENT, AND APPARATUS FOR PERFORMING THE METHOD

[76] Inventor: Jean Guigan, 9, rue Jean Mermoz, 75008 Paris, France

[21] Appl. No.: 790,011

[22] Filed: Oct. 22, 1985

[30] Foreign Application Priority Data

Oct. 26, 1984 [FR] France .............................. 84 16447

[51] Int. Cl.⁴ ............................................ G01N 21/07
[52] U.S. Cl. ...................................... 436/45; 422/64; 422/72; 422/102; 436/179; 436/180
[58] Field of Search ................. 436/174, 179, 180, 45; 422/64, 72, 102

[56] References Cited

U.S. PATENT DOCUMENTS

| | | | |
|---|---|---|---|
| 3,211,368 | 10/1965 | Shanley | 494/17 |
| 3,766,016 | 10/1973 | Guigan | 435/294 |
| 3,770,027 | 11/1973 | Guigan | 141/34 |
| 3,814,582 | 6/1974 | Rohrbaugh et al. | 422/64 |
| 3,890,101 | 6/1975 | Tiffany et al. | 422/72 |
| 3,951,608 | 4/1976 | Trod | 422/64 |
| 4,279,862 | 7/1981 | Bretaudiere et al. | 422/72 |
| 4,412,973 | 11/1983 | Guigan | 422/72 |
| 4,462,964 | 7/1984 | Guigan | 422/102 |
| 4,469,793 | 9/1984 | Guigan | 422/102 |
| 4,632,908 | 12/1986 | Schultz | 422/72 |
| 4,673,653 | 6/1987 | Guigan | 422/64 |

FOREIGN PATENT DOCUMENTS

2503866 10/1982 France .

OTHER PUBLICATIONS

Shultz, Clin. Chem. vol. 31, No. 9, 1985, pp. 1458–1463.

Primary Examiner—Michael S. Marcus
Attorney, Agent, or Firm—Sughrue, Mion, Zinn, Macpeak, and Seas

[57] ABSTRACT

A method of performing medical analysis on a liquid sample makes use of a container (1) made from a single plastics molding, the container is compartmented so as to include a sample storage chamber (4), a calibrated cell (6), and a plurality of storage chambers (40, 50, 60) for liquid reagents. Various centrifuging operations are performed to cause the sample and the reagents to pass successively into an analysis vat (11).

5 Claims, 5 Drawing Sheets

METHOD OF PERFORMING MEDICAL ANALYSIS ON A SAMPLE OF LIQUID BY MEANS OF AT LEAST ONE LIQUID REAGENT, AND APPARATUS FOR PERFORMING THE METHOD

The present invention relates to a method of performing medical analysis on a sample of liquid using at least one liquid reagent.

A first aim of the invention is to provide a method of analyzing a very small sample of liquid, e.g. a few microliters. This is particularly advantageous in medical analysis since it is then possible, for example, to avoid taking blood from patients by means of syringes and to make do with a few drops of blood taken from the end of a finger.

Another aim of the invention is to provide a method enabling numerous presently required medical analyses (of which there are about three hundred) to be performed using a maximum of four different reagents.

A final aim of the invention is to provide a method which is cheap and simple for the operator who makes use of containers which are stored containing liquid reagents. This is made possible by the fact that the liquid reagents have an entirely satisfactory shelf life (from eighteen months to two years).

SUMMARY OF THE INVENTION

The present invention provides a method of performing medical analysis on a sample of liquid by means of at least one liquid reagent, the method including the improvements whereby a compartmented container is used which container includes:

- a storage chamber for said liquid sample, said chamber being connected by a capillary duct to one end of a calibrated cell whose other end is connected via a capillary duct to an overflow chamber; and
- a plurality of storage chambers for liquid reagents disposed around a pouring chamber, said pouring chamber being connected via respective capillary ducts extending in various orientations to said calibrated cell and to said reagent storage chambers, and also communicating with an analysis vat.

Said container is closed by a lid which is fitted both with a sample storing receptable which communicates directly with said sample storage chamber and which is situated thereabove, and with a removable stopper which enters into said pouring chamber to close the ends of said capillary ducts communicating therewith.

Means are provided to position said container on the turntable of a centrifuge in a plurality of predetermined positions which differ from one another by rotations of the container about its own axis, relative to the turntable and through a given angle.

According to the method, liquid reagents are initially disposed in respective ones of said reagent storage chambers, said sample is inserted into said sample storing receptacle and then flows under gravity into said sample storage chamber, said stopper is then removed and said container is placed on said centrifuge turntable in order to perform a plurality of centrifuging operations in succession, with the angular position of the container relative to the direction of centrifugal force being selected each time from said predetermined positions and as a function of the orientation of the capillary duct concerned so as to cause said sample to pass successively from said sample storage chamber into said calibrated cell, and then from said calibrated cell into said pouring chamber and into said analysis vat, and then to cause each reagent to pass from its storage chamber into said pouring chamber and into said analysis vat.

In particularly advantageous implementation of the method, said predetermined positions of the container are separated from one another by angles of about 90° and about 180°, which correspond substantially to the angles between said capillary ducts communicating with said pouring chamber.

The present invention also provides apparatus for performing the above-defined method. The apparatus comprises a flat cylindrical container made of plastics material with a diameter of about 3 centimeters and having internal compartments so as to include:

- a storage chamber for said liquid sample, which chamber is connected via a capillary duct to one end of a calibrated cell whose other end is connected via a capillary duct to an overflow chamber;
- a plurality of chambers for storing liquid reagents disposed around a pouring chamber, said pouring chamber being connected via respective capillary ducts at different orientations to said calibrated cell and to said reagent storing chambers, and also communicating with an analysis vat.

The said container is made from a single molded part. The capillary ducts have diameters of about 2 tenths of a millimeter.

The container is closed by a lid of plastics material which is provided with a sample storing receptacle communicating directly with said sample storage chamber and situated thereabove. The lid also has a chimney situated above said pouring chamber and intended to receive a stopper capable of closing all the orifices opening into said pouring chamber. The chimney, said receptacle, and the remainder of the lid are constituted by a single piece of molded plastics material.

In a particularly advantageous embodiment, the capillary ducts providing communication between the pouring chamber and said calibrated cell and between the pouring chamber and one of the reagent storage chambers are parallel to each other. The capillary ducts providing communication between two other reagent storage chambers and the pouring chamber are diametrically opposed relative to the pouring chamber and at an angle which is substantially equal to 90° relative to the two above-mentioned capillary ducts.

The said pouring chamber advantageously includes internal ribs constituting deflectors for preventing the reagent taken from one storage chamber from penetrating into another storage chamber.

BRIEF DESCRIPTION OF THE DRAWINGS

An embodiment of the invention is described by way of example with reference to the accompanying drawings in which.

MORE DETAILED DESCRIPTION

FIGS. 1 to 8 show a container 1 made of plastics material which is generally flat and cylindrical in shape and which is closed by a lid 2 of plastics material. By way of example, the container has a diamater of about 3 centimeters.

Figure 1:
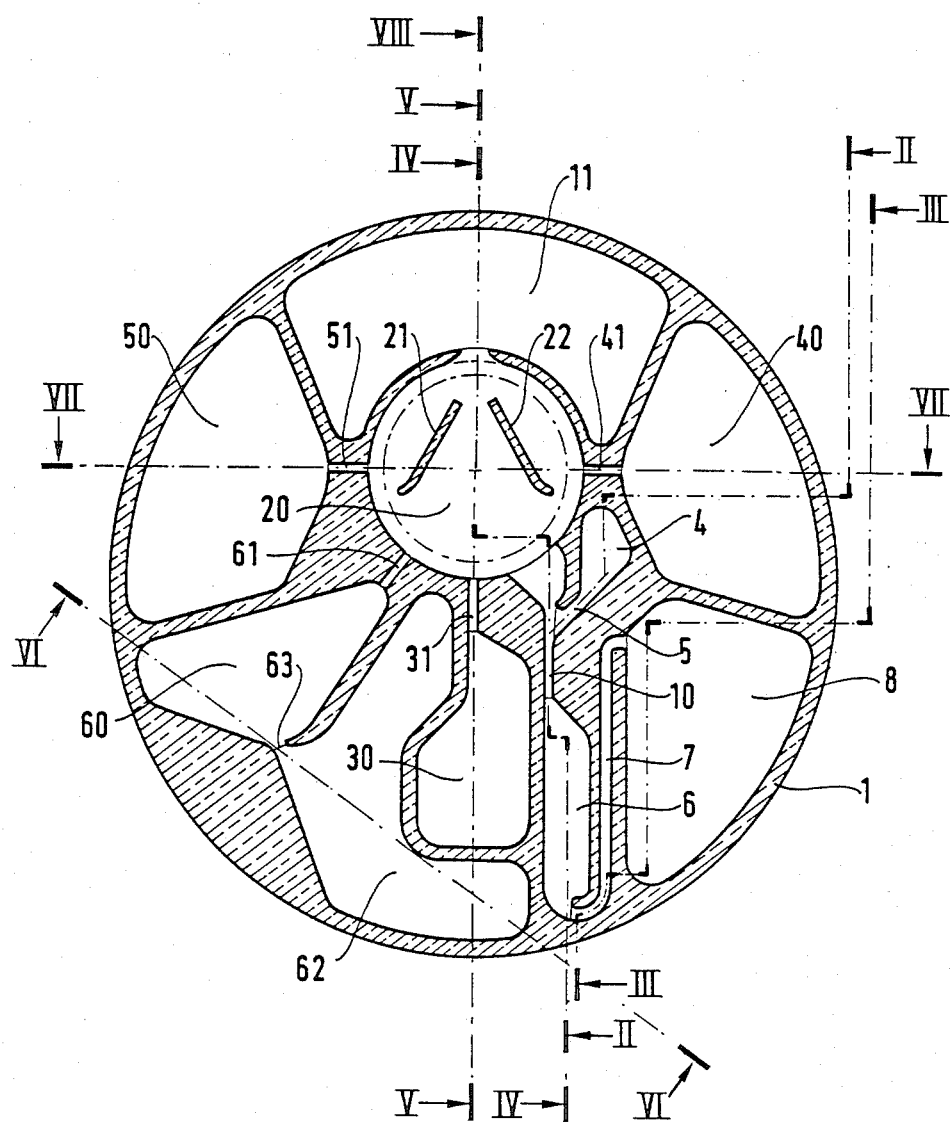
FIG. 1 is a plan view of the container without its lid.
Figure 2:
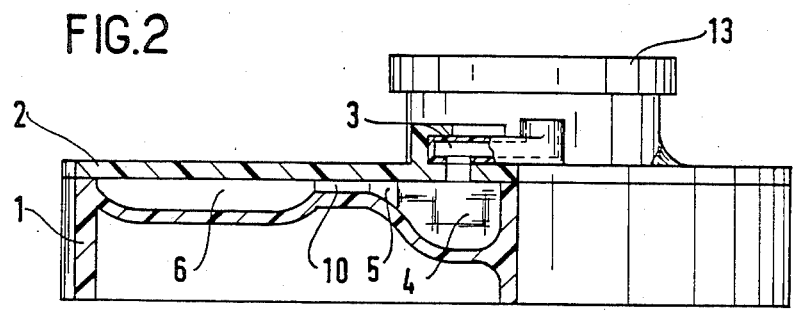
FIGS. 2 to 8 are sections through the container taken on lines II—II to VIII—VIII respectively in FIG. 1.
Figure 3:
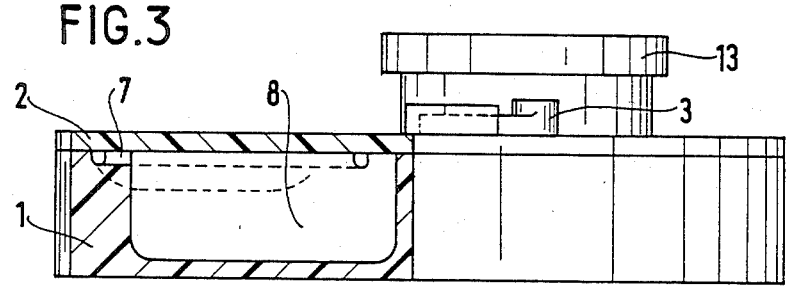
Figure 4:
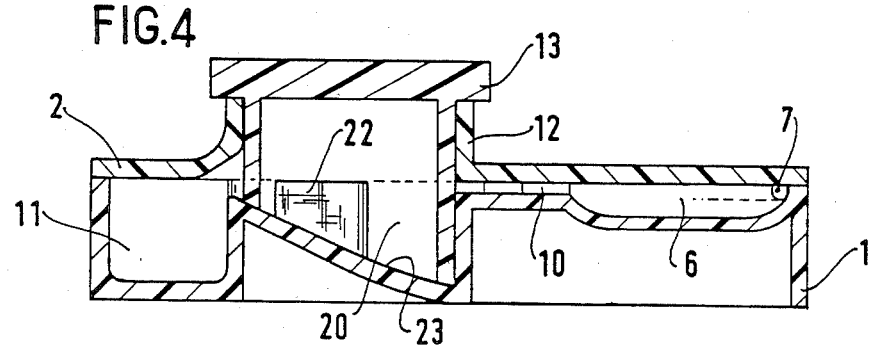
Figure 5:
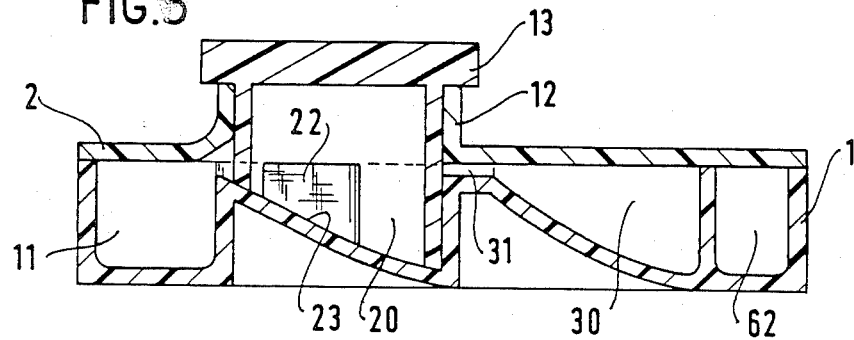
Figure 6:
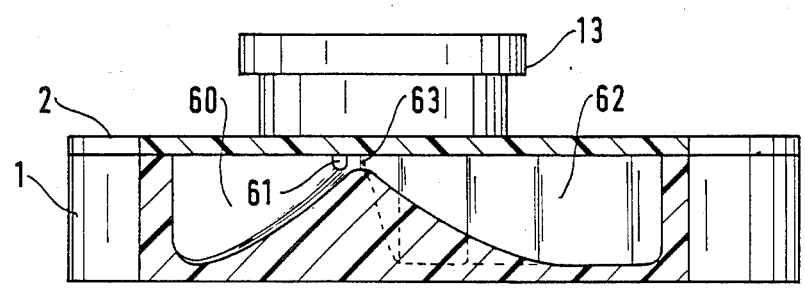
Figure 7:
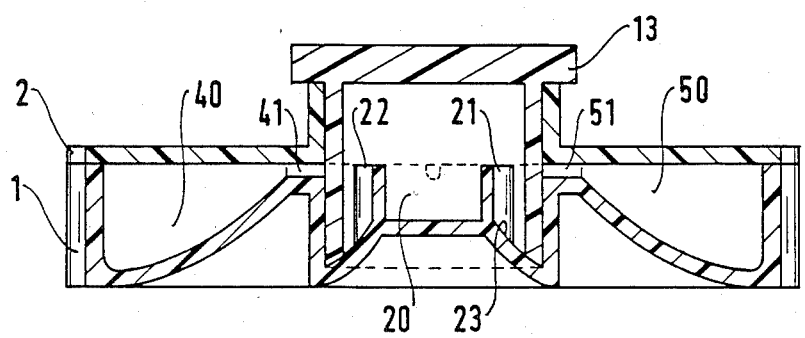
Figure 8:
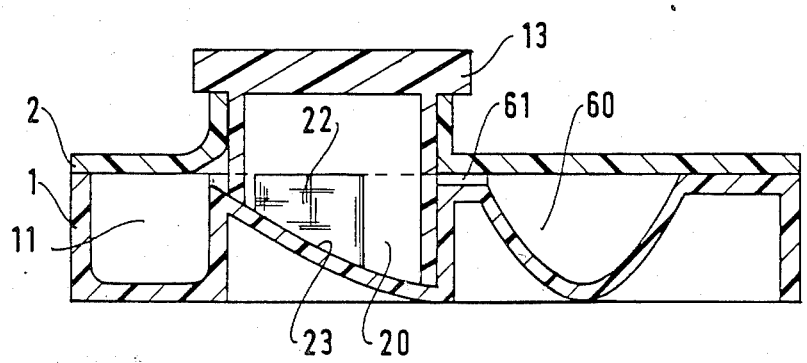

FIGS. 1 and 2 show that the top portion of the lid 2 bears a storage receptacle 3 for storing a sample of liquid and communicating directly with chamber 4 for storing a liquid sample inside the container.

The storage chamber 4 is connected via a capillary duct 5 to a calibrated chamber 6 which communicates via a capillary duct 7 with an overflow chamber 8 and via a capillary duct 10 with a pouring chamber 20. The pouring chamber has deflector ribs 21, 22 and communicates with an analysis vat 11 over the top portion of a common wall 23.

The container also includes a plurality of storage chambers for liquid reagents, for example there is a chamber 30 which communicates with the pouring chamber 20 via a capillary duct 31. It may be observed that the capillary ducts 10 and 31 are substantially parallel to each other. Two other reagent storage chambers referenced 40 and 50 communicate with the pouring chambers 20 via respective capillary ducts 41 and 51 which are diametrically opposed relative to the pouring chamber and which are oriented at substantially 90° relative to the said capillary ducts 10 and 31. Finally, there is a fourth reagent storage chamber comprising two compartments 60 and 62 which communicate with each other via an orifice 63. Only the compartment 60 is in communication with the pouring chamber 20 via a capillary duct 61. This duct is at an angle of substantially 45° to the ducts 10, 31, 41, and 51.

The lid 2 has a chimney 12 mounted thereon above the pouring chamber 20 and suitable for receiving a stopper 13. Throughout the period during which the container is stored together with the reagents that it contains, the stopper 13 serves to close the orifices opening out into the pouring chamber 20 (and in particular the orifices from the capillary ducts 31, 41, 51, and 61).

FIGS. 9 to 20 are plan views of the device shown in FIGS. 1 to 8 as seen from above while the method in accordance with the invention is being implemented.

Figure 9:
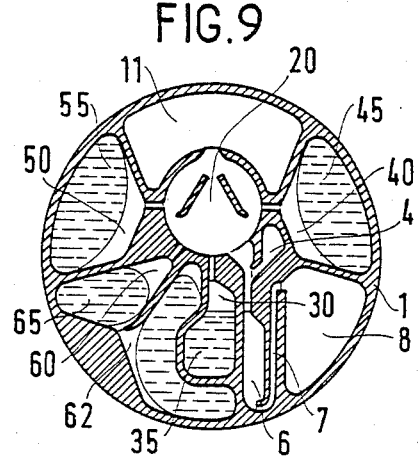
FIGS. 9 to 20 are diagrams showing the various positions of the container containing its sample and reagents during various steps of the method in accordance with the invention.
Figure 10:
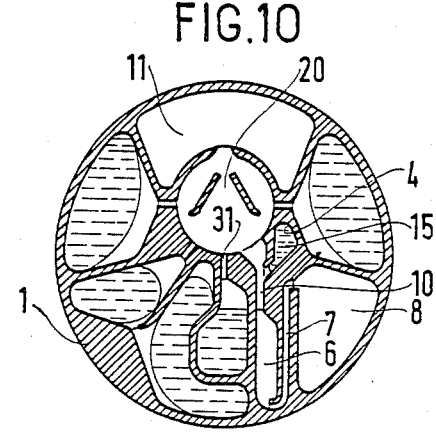
Figure 11:
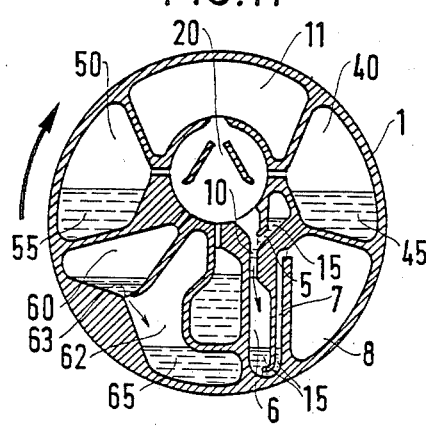
Figure 12:
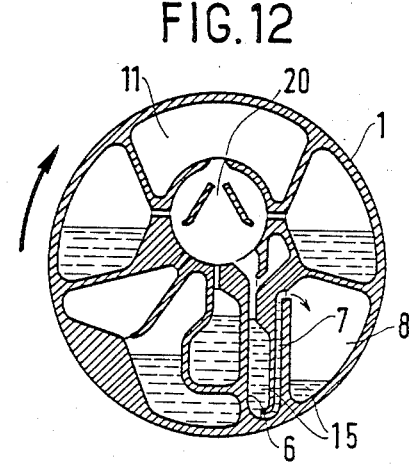
Figure 13:
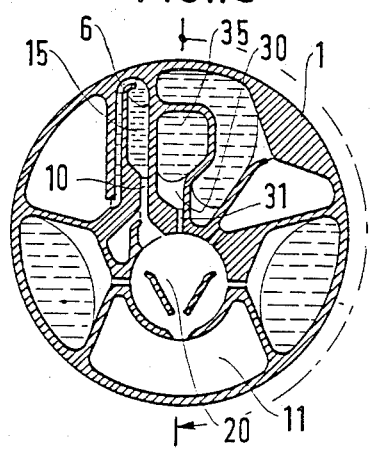

FIG. 9 shows the initial stage when the chambers 30, 40, 50, 60, and 62 of the container 1 are respectively filled with reagents 35, 45, 55, and 65.

The container 1 is then placed on the turntable of a centrifuge. It will readily be understood that a dozen or so containers of this type may be placed in a circle on the turntable.

The center of rotation of the turntable is situated so that the end of the cell 6 which is connected to the capillary duct 7 is situated further from the center of rotation than is the end of the cell 6 which is connected to the duct 10. The direction of centrifugal force is substantially aligned with the capillary ducts 10 and 31.

At this moment, the stopper 13 is removed and a drop of several microliters of sample 15 is inserted into the receptacle 3. The sample 15 ends up in the storage chamber 4 (see FIG. 10).

A first centrifuging operation is then performed and an intermediate stage (FIG. 11) and the final stage (FIG. 12) thereof are shown in the drawings. The sample 15 passes into the calibrated cell 6 and into the capillary duct 7. When the calibrated cell 6 is filled with the sample 15, any excess sample ends up in the overflow chamber 8.

The container is then rotated through 180° about its own axis (see FIG. 13) so that the capillary ducts 10 and 13 are still parallel to the direction of centrifugal force.

Figure 14:
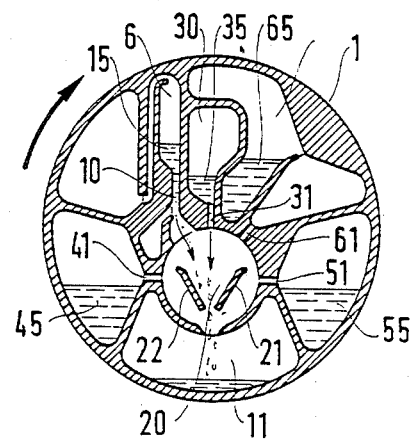
Figure 15:
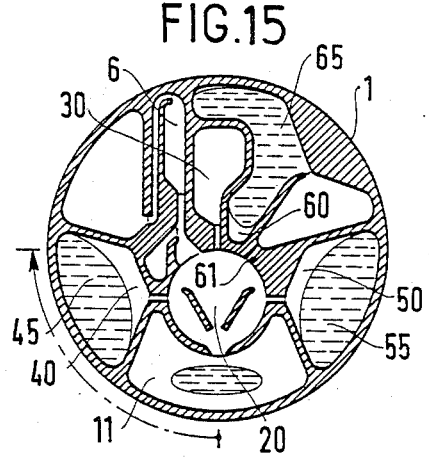

A second centrifuging operation is then performed (see FIGS. 14 and 15). The sample 15 passes along the capillary duct 10 into the pouring chamber 20 and then into the analysis vat 11. Simultaneously, the reagent 35 passes along the capillary duct 31 into the pouring chamber 20 and into the vat 11. The orientation of the capillary ducts 41, 51, and 61 relative to the centrifugal force is such that other reagents remain captive in their respective storage chambers. FIG. 15 shows the container at rest after the second centrifuging operation. Both the calibrated cell 6 and the storage chamber 30 are empty. It may also be observed that the first centrifuging operation (FIGS. 11 and 12) have the effect of causing all of the reagent 65 to move into the compartment 62 which does not communicate with the pouring chamber, and that this state of affairs remains unchanged during the second centrifuging operation.

Figure 16:
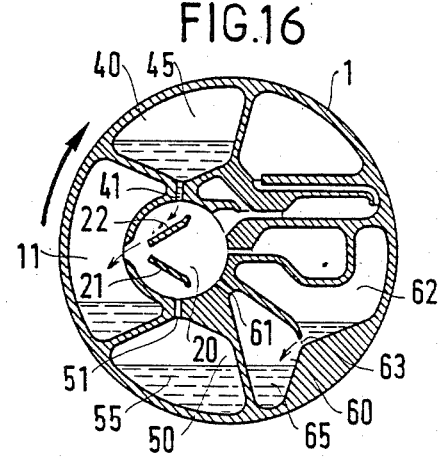
Figure 17:
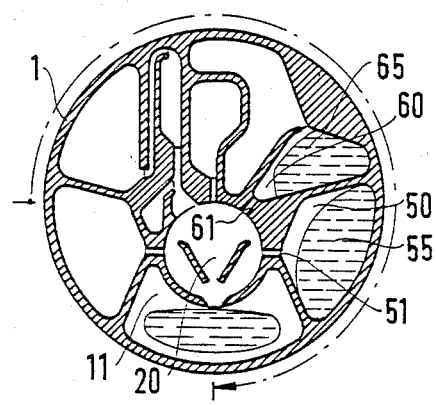
Figure 18:
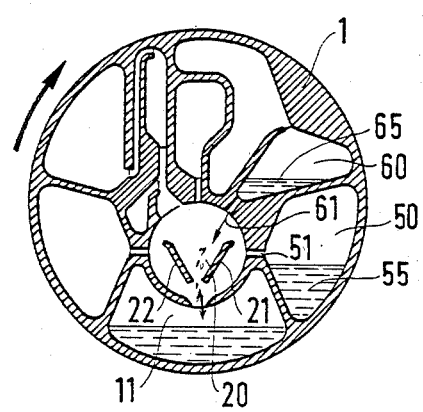
Figure 19:
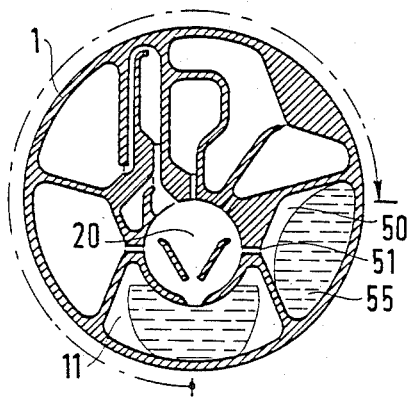
Figure 20:
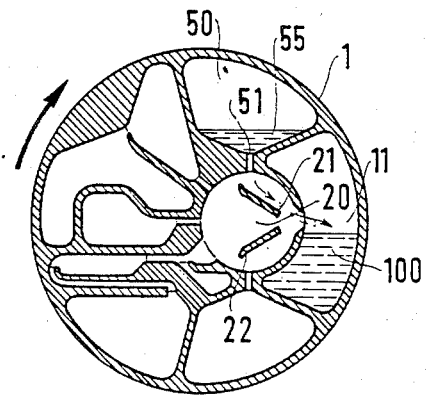

The container 1 is then rotated through 90° about its own axis as can be seen in FIG. 16. The capillary ducts 51 and 41 are then parallel to the direction of centrifugal force, but a third centrifuging operation has the effect of emptying only the reagent 45 into the pouring chamber 20 and thus into the analysis vat 11. The reagent 45 is deflected by the rib 22 towards the vat 11 and there is no risk of it penetrating into the chamber 50. The reagent 65 moves from the compartment 62 into the compartment 60 which is in communication with the pouring chamber 20.

As can be seen in FIG. 17, the container is again rotated through 90° about its own axis. The direction of the capillary duct 51 is then such that only the reagent 65 is capable of being moved into the pouring chamber 20 during a fourth centrifuging operation (see FIGS. 18 and 19).

Finally, the container 1 is rotated a last time through 90° about its own axis thus placing the capillary duct 51 in such a manner that a fifth centrifuging operation empties the reagent 55 into the vat 11, thus providing a mixture 100.

The reaction which occurs in this mixture may be observed by any suitable means.

The device described is capable of performing analysis requiring four liquid reagents. However, some analyses require only one, two or three reagents, in which case some of the reagent-storing chambers may be left empty. Alternatively different types of container may be provided having different numbers of storage chambers.

I claim:

1. A method of performing medical analysis on a sample a liquid by means of at least one liquid reagent using a compartmented container, said container comprises: a sample storage receptacle,
   a storage chamber for a liquid sample, connected to said storage receptacle,
   a calibrated cell,
   an overflow chamber,
   an analysis vat,
   a capillary duct connecting said storage chamber to one end of said calibrated cell,
   a capillary duct connecting the other end of said calibrated cell to said overflow chamber;

a plurality of storage chambers for liquid reagents, disposed around a pouring chamber, capillary ducts extending in different angular orientations to each other and connecting said pouring chamber to said calibrated cell and to said reagent storage chambers, means communicating said pouring chamber to said analysis vat;

a lid closing off said container, said lid being fitted both with said sample storage receptacle which communicates directly with said sample storage chamber and which is situated there above, and with a removable stopper which enters into said pouring chamber and closes orifices defined by the ends of said capillary ducts communicating therewith; and means to position said container on a turntable of a centrifuge with the container axis offset from the axis of rotation of said turntable and in a plurality of predetermined positions which differ from one another by rotations of the container about its own axis, relative to the turntable and through a given angle;

said method comprising the steps of:

initially disposing liquid reagents in respective ones of said reagent storage chambers, inserting said sample into said sample storage receptacle and then flowing said sample under gravity into said sample storage chamber, removing said stopper and placing said container on said centrifuge turntable and performing a plurality of centrifuging operations in succession, with the angular position of the container relative to the direction of centrifugal force being selected each time from said predetermined positions and as a function of the angular orientation of the capillary duct concerned so as to cause said sample to pass successively from said sample storage chamber into said calibrated cell, and then from said calibrated cell into said pouring chamber and into said analysis vat, and then to cause each reagent to pass from its storage chamber into said pouring chamber and into said analysis vat.

2. A method according to claim 1, wherein said predetermined positions of the container are separated from one another by angles of about 90° and about 180°, which angles correspond substantially to the angles between said capillary ducts communicating with said pouring chamber.

3. Apparatus for performing medical analysis on a sample of liquid by means of at least one liquid reagent, said apparatus comprising a single-piece container made of molded plastics material and closed by a single-piece lid made of molded plastics material, said container being internally subdivided into compartments including:

a storage chamber for a liquid sample, a calibrated cell, an overflow chamber, an analysis cell, a plurality of storage chambers, a pouring chamber surrounded by said plurality of storage chambers, a plurality of capillary ducts, one of said capillary ducts connecting said storage chamber to the end of said calibrated cell, another of said capillary ducts connecting the other end of said calibrated cell to said overflow chamber;

others of said capillary ducts extending in different angular orientations to each other and connecting said pouring chamber to said calibrated cell and to said reagent storing chambers, and further means communicating said pouring chamber to said analysis vat; and said lid being provided with a sample storing receptacle communicting directly with said sample storage chamber and situated thereabove, and also with a chimney situated above said pouring chamber and receiving a stopper closing all orifices defined by the ends of ones of said capillary ducts opening into said pouring chamber.

4. Apparatus according to claim 3, wherein said container is generally flat and cylindrical, having a diameter of about 3 centimeters, and wherein said capillary ducts have a diameter of about 2 tenths of a millimeter.

5. Apparatus according to claim 3, wherein said reagent storage chambers contain respective liquid reagents.

* * * * *